United States Patent [19]

Paulus et al.

[11] 4,120,686
[45] Oct. 17, 1978

[54] COMPOSITION FOR COMBATING SLIMES

[75] Inventors: Wilfried Paulus; Hermann Genth, both of Krefeld, Germany

[73] Assignee: Bayer Aktiengesellschaft, Leverkusen, Germany

[21] Appl. No.: 692,171

[22] Filed: Jun. 2, 1976

[30] Foreign Application Priority Data

Jun. 28, 1975 [DE] Fed. Rep. of Germany ....... 2528994

[51] Int. Cl.$^2$ .............................................. A01N 9/02
[52] U.S. Cl. ....................................... 71/67; 162/161; 424/286
[58] Field of Search ............................ 71/67; 162/161

[56] References Cited

PUBLICATIONS

Bundesgesundheitsblatt, 14, No. 6/7, pp. 83 to 86, (1971).
Kamitani et al., Chem. Abst., vol. 64 (1966), 9941h.

*Primary Examiner*—Catherine L. Mills

*Attorney, Agent, or Firm*—Burgess, Dinklage & Sprung

[57] ABSTRACT

Composition for combating slimes containing as the active compound combination, tetramethylthiuram disulfide and aroyl-ethyl-ammonium salts having the formula

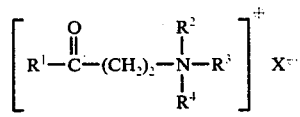

wherein $R^1$ is optionally monosubstituted or polysubstituted aromatic, carbocyclic or heterocyclic, radical and $R^2$, $R^3$ and $R^4$ are the same or different and are optionally monosubstituted or polysubstituted aliphatic or aromatic carbocyclic or form, together with 4 to 6 hydrocarbon members, a heterocyclic ring, and X is an anion of an inorganic or organic acid.

4 Claims, No Drawings

COMPOSITION FOR COMBATING SLIMES

BACKGROUND

This invention relates to new synergistic active compound combinations of aroyl-ethyl-ammonium salts and tetramethylthiuram disulphide for combating slimes.

It has already been disclosed that aroyl-ethyl-ammonium salts can be used for preserving aqueous systems (tetramethylthiuram disulphide is known as an agent for combating slimes (Bundesgesundheitsbl. 14, No. 6/7, pages 83 to 86, 1971).

However, when used by themselves against slimes, these compounds are of little effect, particularly if low amounts and low concentrations are used.

SUMMARY

It has now been found that the combination of an aroyl-ethyl-ammonium salt of the formula

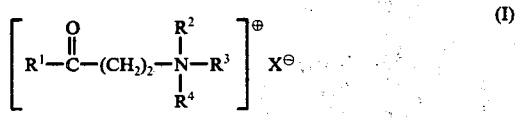 (I)

wherein $R^1$ represents an optionally monosubstituted or polysubstituted aromatic, carbocyclic or heterocyclic radical and $R^2$, $R^3$ and $R^4$ are identical or different and represent an optionally monosubstituted or polysubstituted aliphatic or aromatic carbocyclic radical or form, together with 4 to 6 hydrocarbon members, a heterocyclic ring, and X represents an anion of an inorganic or organic acid, and tetramethylthiuram disulphide has a particularly high activity in combating slimes.

DESCRIPTION

Surprisingly, the effectiveness of the active compound combinations according to the invention in combating slimes is substantially greater than the sum of the effects of the individual active compounds. Accordingly, one is dealing with a genuine synergistic effect. The active compound combinations represent a valuable enrichment of the art.

An optionally monosubstituted or polysubstituted aromatic carbocyclic radical $R^1$ can be a radical with 5 to 18, preferably 6 to 10, carbon atoms, such as the phenyl, naphthyl, phenanthracyl, tetracyl, anthracyl and biphenyl radical, preferably the phenyl and naphthyl radical.

An optionally monosubstituted or polysubstituted heterocyclic radical $R^1$ can be a 5-membered or 6-membered ring, which in addition to hydrocarbon members contains one or more hetero-atoms, such as, for example, nitrogen, oxygen and/or sulphur. The heterocyclic radical can furthermore be fused to one or more radicals of the benzene series. The following heterocyclic radicals may be mentioned as examples: the pyrole, furane, thiophene, indole, cumarane, thionaphthene, pyridine, pyrone, oxazole, imidazole, benzoxazole, benzimidazole, benzthiazole, quinoline, isoquinoline, piperidine, pyrrolidine, thiazole, pyrazole and tetrahydrofurane radical, the pyridine, thiophene, thiazole and pyrazole radical being preferred.

Optionally monosubstituted or polysubstituted aliphatic radicals $R^2$, $R^3$ and $R^4$ which may be mentioned are those with 1 to 6 carbon atoms, such as methyl, ethyl, propyl, iso-propyl, butyl, iso-butyl, pentyl, iso-pentyl, hexyl and iso-hexyl, preferably methyl and ethyl.

Optionally monosubstituted or polysubstituted aromatic carbocyclic radicals $R^2$, $R^3$ and $R^4$ which may be mentioned are those with 5 to 18 carbon atoms, such as the phenyl, naphthyl, phenanthracyl, tetracyl, anthracyl and biphenyl radical, preferably the phenyl and naphthyl radical.

The optionally monosubstituted or polysubstituted heterocyclic radicals which can be formed by joining the radicals $R^2$, $R^3$ and $R^4$ by 4 to 6 hydrocarbon members can be aromatic or fully or partially hydrogenated. They can furthermore be fused to one or more radicals of the benzene series or form a part of the hexamethylenetetramine or tetraazatricyclo-[6,2,1,1]-dodecane skeleton. The following heterocyclic radicals may be mentioned as examples: pyridine, imidazole, benzimidazole, quinoline, isoquinoline, piperidine, thiazole, hexamethylenetetramine and tetraazatricyclo-[6,2,1,1]-dodecane. The pyridine, thiazole, hexamethylenetetramine and tetraazatricyclo-[6,2,1,1]-dodecane radical are preferred.

Examples which may be mentioned of substituents of the radicals $R^1$, $R^2$, $R^3$ and $R^4$ are the halogens, such as fluorine, chlorine, bromine and iodine, the hydroxyl group, the nitro group, a straight-chain or branched $C_1$–$C_6$-alkyl radical, such as methyl, ethyl, propyl, iso-propyl, butyl, iso-butyl, pentyl, iso-pentyl, hexyl and iso-hexyl, and a straight-chain or branched alkoxy or halogenoalkyl radical, with alkyl and halogen in each case having the range of meanings mentioned above.

Examples which may be mentioned of anions X of an inorganic or organic acid are chloride, bromide, iodide, sulphate, nitrate, acetate and methoxysulphonate, preferably chloride.

The aroyl-ethyl-ammonium salts which can be used for the active compound according to the invention are known (Chem. Ber. 88, 1027 (1955) and German Published Specification No. 2,034,540). The following aroyl-ethyl-ammonium salts may be mentioned as examples: (2-benzoyl-)ethyl-trimethyl-ammonium chloride, (2-benzoyl-)ethyl-trimethyl-ammonium-methyl-sulphate, N-(2-benzoyl-)ethyl-hexaminium chloride, N-(2-benzoyl-)ethyl-tetraazoniumtricyclododecane chloride, (2-p-chlorobenzoyl-)ethyl-trimethyl-ammonium chloride, N-(2-p-chlorobenzoyl-)ethyl-hexaminium chloride, N-(2-p-chlorobenzoyl-)ethyl-tetraazoniumtricyclododecane chloride, N-(2-p-methylbenzoyl-)ethyl-hexaminium chloride, N-(2-p-methoxybenzoyl-)ethyl-hexaminium chloride, N-(2-p-nitrobenzoyl-)ethyl-hexaminium chloride, N-(2-p-isopropylbenzoyl-)ethyl-hexaminium chloride, N-(2-dichlorobenzoyl-)ethyl-hexaminium chloride, N-(2-naphthoyl-)ethyl-hexaminium chloride, (2-naphthoyl-)ethyl-trimethyl-ammonium chloride, N-(2-p-chlorobenzoyl-)ethyl-N-methyl-pyrrolidinium chloride, N-(2-p-chlorobenzoyl-)ethyl-pyridinium chloride, N-(2-p-chlorobenzoyl-)ethyl-(4,5-dimethyl-)thiazolium chloride, N-(2-p-chlorobenzoyl-)ethyl-isoquinolinium chloride, N-(2-thienoyl-)ethyl-hexaminium chloride and (2-benzoyl-)ethyl-benzyl-dimethyl-ammonium chloride.

The active compound tetramethylthiuram disulphide is known and can be prepared according to Ber. dtsch. chem. Ges., 35, 820 (1902).

The weight ratios of the groups of active compound in the active compound combinations can vary within relatively wide ranges. In general, 0.01 to 99, preferably 0.1 to 9, and particularly preferentially 0.5 to 2, parts by weight of tetramethylthiuram disulphide are present per part by weight of aroyl-ethyl-ammonium salt.

Combinations of 40 to 52 parts by weight of aroyl-ethyl-ammonium chloride and 60 to 48 parts by weight of tetramethylthiuram disulphide are particularly effective.

The active compound combinations according to the invention have a powerful action on slime-forming micro-organisms. Examples of micro-organisms which may be mentioned are bacteria, fungi and algae which cause slime formation.

Examples which may be mentioned of micro-organisms which are subject to the action of the combinations according to the invention are *Aerobacter aerogenes, Chaetomium globosum Kunze, Stichococcus bacillaris Naegeli, Euglena gracilis Klebs, Chlorella pyrenoidosa Chick, Phormidium foredorum Gromont, Oscillatoria geminata Meneghini, Phaedodactylum tricornutum Bohlin, Penicillium expansum* and *Aspergillus niger*.

Slime-forming micro-organisms are frequently found in cooling water circuits or pulp feed channels in the manufacture of paper and fibres. The systems frequently contain organic compounds and trace elements which act as a nutrient source for the micro-organisms, and are at a temperature which promotes the growth of the micro-organisms.

The new active compound combinations are in general used in the form of a powder.

The suitable concentration of the active compound combinations depends on the nature and occurrence of the slimes produced, the germ count and the nature and temperature of the medium. The optimum use concentration must in each case be determined by series of tests.

Slime formation in cooling water circuits or pulp feed channels causes blockages of pipelines, microbiological corrosion due to formation of acid metabolism products, reduction of cooling efficiency, lowering of product quality and interference with production.

The abovementioned disadvantages are avoided in an advantageous manner by using the active compound combinations according to the invention.

Known agents for combating slimes, such as, for example, compounds which eliminate chlorine (for example chlorine dioxide) have a limited spectrum of action whilst those such as, for example, chlorinated phenols (for example pentachlorophenol) cause effluent problems because of their poor biological degradability (Wochenblatt für Papierfabrikation 91, No. 9, 419 to 425 (1963)).

In contrast, the active compound combinations according to the invention have the advantage of possessing a broad spectrum of action and good biological degradability. This permits their use in open cooling water circuits and process water circuits.

The active compound combinations according to the invention advantageously permit replacing the previously available agents for combating slimes by more effective agents and reducing the amount of biocide required for combating slimes.

EXAMPLES 1 TO 4

Substance A: N-(2-Chlorobenzoyl-ethyl)-hexaminium chloride

Substance B: Tetramethylthiuram disulphide

The substances A and B are combined in various mixing ratios and the mixtures are tested for synergistic action in accordance with the test method given below.

Test method:

Concentration series were prepared from the aroyl-ethyl-ammonium salt (A) and tetramethylthiuram disulphide (B) in a liquid nutrient medium (boullion), which was infected with the test bacterium *Aerobacter aerogenes*. After 4 days' incubation, the lowest concentration of each mixture which prevents growth of the test bacterium (clear nutrient solution) is recorded as the minimum inhibitory concentration (MIC). The growth of the test bacterium manifests itself in a turbidity of the nutrient solution. The MIC values of the various mixtures are compared with the MIC values of the components of the mixture (A and B). The synergism effect is determined by the method of Kull (Applied Microbiol. 9, 538 to 541 (1961)). The following equation applies:

$$(Q_A/Q_a) + (Q_B/Q_b) = X$$

$X = 1$ denotes additive behavior $X = >1$ denotes antagonism $X = <1$ denotes synergism $Q_a$ = concentration of the substance A which represents the MIC $Q_b$ = concentration of the substance B which represents the MIC $Q_A$ = amount of substance A in the mixture, which prevents growth of the bacterium $Q_B$ = amount of substance B in the mixture, which prevents growth of the bacterium The result of the test is recorded in Table 1: The notes A/B=100/0 and AB=0/100 are given for the purpose of comparison.

Table 1

| Example No. | Weight ratio A/B | MIC values in mg/l | $Q_A$ | $Q_B$ | $\frac{Q_A}{Q_a}$ | $\frac{Q_B}{Q_b}$ | X |
|---|---|---|---|---|---|---|---|
| (Comparative) | 100/0 | 40 | 40 | 0 | — | — | — |
| 1 | 93/7 | 10 | 9.3 | 0.7 | 0.23 | 0.35 | 0.58 |
| 2 | 52/48 | 10 | 5.2 | 4.8 | 0.13 | 0.24 | 0.37 |
| 3 | 40/60 | 10 | 4.0 | 6.0 | 0.10 | 0.30 | 0.40 |
| 4 | 8/92 | 10 | 0.8 | 9.2 | 0.02 | 0.46 | 0.48 |
| (Comparative) | 0/100 | 20 | 0 | 20 | — | — | — |

The data of Table 1 show that the active compound combinations according to the invention are substantially more suitable for preventing the growth of the bacteria than are the individual compounds. Furthermore, it becomes clear that the synergism extends over the entire range of possible mixing ratios.

EXAMPLE 5

A nutrient solution according to Allen (Arch. Mikrobiol. 17, 34 to 53 (1952)) is mixed with 1% of caprolactam as an additional source of carbon and of nitrogen, and is sterilised and then infected with slime organisms which are isolated from the spinnng water circuits used in the manufacture of the polyamide. To demonstrate the synergistic effect, N-(2-chlorobenzoyl-ethyl)-hexaminium chloride (A), or tetramethylthiouram disulphide (B), or an active compound combination consisting of 62 parts by weight of A and 38 parts by weight of B, are added to the nutrient solution. The MIC is determined as the concentration at which the growth of the test organisms after 3 weeks' incubation at room temperature is prevented.

Table 2

| Example No. | Weight ratio A/B | MIC values in mg/l | $Q_A$ | $Q_B$ | $\frac{Q_A}{Q_a}$ | $\frac{Q_B}{Q_b}$ | X |
|---|---|---|---|---|---|---|---|
| (Comparative) 5 | 100/0 | 5 | 5 | 0 | — | — | — |
| | 62/38 | 8 | 3.1 | 1.9 | 0.39 | 0.05 | 0.44 |
| (Comparative) | 0/100 | 40 | 0 | 40 | — | — | — |

EXAMPLE 6

An agar which contains beer wort and peptone is infected with *Chaetomium globosum Kunze*. To demonstrate the synergistic effect, the agar has added to it N-(2-chlorobenzoyl-ethyl)-hexaminium chloride (A), or tetramethylthiuram disulphide (B), or an active compound combination of 62 parts by weight of A and 38 parts by weight of B. The concentration of active compound which, after 14 days' incubation at 28° C. and 60 to 70% relative humidity, prevents the growth of the test fungus is recorded as the MIC. The synergistic effect is shown in Table 3:

Table 3

| Example No. | Weight ratio | MIC values | $Q_A$ | $Q_B$ | $\frac{Q_A}{Q_a}$ | $\frac{Q_B}{Q_b}$ | X |
|---|---|---|---|---|---|---|---|
| (Comparative) | 100/0 | 500 | 500 | 0 | — | — | — |
| 6 | 62/38 | 50 | 31 | 19 | 0.06 | 0.38 | 0.44 |
| (Comparative) | 0/100 | 50 | 0 | 50 | — | — | — |

EXAMPLE 7

A mixture culture of green algae, blue algae, brown algae and diatoms (*Stichococcus bacillaris Naegeli, Euglena gracilis Klebs, Chlorella pyrenoidosa Chick, Phormidium foredarum Gromont, Oscillatoria geminata Meneghini* and *Phaedodactylum tricornutum Bohlin*) is introduced into a nutrient solution according to Allen (Arch. Mikrobiol. 17, 34 to 53 (1952)), through which air is allowed to bubble. After 2 weeks, the nutrient solution is colored deep green-blue, as a result of intensive growth of algae. To demonstrate the synergistic effect, the nutrient solution has added to it N-(2-chlorobenzoyl-ethyl)-hexaminium chloride, or tetramethylthiuram disulphide (B) or, in a further test series, an active compound combination of 62 parts by weight of A and 38 parts by weight of B. The concentration at which the algae die off (the nutrient solution is decolorized) is taken as the mean lethal concentration (MLC). The synergistic effect is shown in Table 4:

Table 4

| Example No. | Weight ratio A/B | MLC values in mg/l | $Q_A$ | $Q_B$ | $\frac{Q_A}{Q_a}$ | $\frac{Q_B}{Q_b}$ | X |
|---|---|---|---|---|---|---|---|
| (Comparative) 7 | 100/0 | 85 | 85 | 0 | — | — | — |
| | 62/38 | 50 | 31 | 19 | 0.36 | 0.19 | 0.55 |
| (Comparative) | 0/100 | 100 | 0 | 100 | — | — | — |

EXAMPLE 8

The back water from a papermaking machine which produces crepe paper for hand towels, contains about $10^8$ micro-organisms per ml (slime-forming bacteria and fungi). The germ count in the back water can be reduced by more than 99.99% if 20 mg per liter of back water of an active compound combination of 62 parts by weight of N-(2-p-chlorobenzyl-ethyl)-hexaminium chloride (A) and 38 parts by weight of tetramethylthiuram disulphide (B) are added. In Table 5, K indicates the concentration which reduces the germ count in the back water by 99.99%. In Table 5, the active compound combination is also compared with the pure compounds A and B, and the synergism is determined.

Table 5

| Example No. | Weight ratio A/B | K in mg/l | $Q_A$ | $Q_B$ | $\frac{Q_A}{Q_a}$ | $\frac{Q_B}{Q_b}$ | X |
|---|---|---|---|---|---|---|---|
| (Comparative) | 100/0 | 30 | 30 | 0 | — | — | — |
| 8 | 62/38 | 20 | 12.4 | 7.6 | 0.41 | 0.06 | 0.47 |
| (Comparative) | 0/100 | 120 | 0 | 120 | — | — | — |

EXAMPLES 9 TO 24

Mixtures of the following substance (A) with tetramethylthiuram disulphide (B) are tested for their synergistic action analogously to Example 1:

Examples 9 to 12: (2-Benzoyl)-ethyl-trimethyl-ammonium chloride

Examples 13 to 16: N-(2-p-Chlorobenzoyl-)ethyl-N-methyl-pyrrolidinium chloride

Examples 17 to 20: N-(2-p-Chlorobenzoyl-)ethyl-pyridinium chloride

Examples 21 to 24: (2-Benzoyl-)ethyl-trimethyl-ammonium iodide

The results are summarized in the table in which X denotes the synergism of the systems tested:

| Weight ratio A/B | Ex. No. | X | Ex. No. | X | Ex. No. | X | Ex. No. | X |
|---|---|---|---|---|---|---|---|---|
| 100/0 | — | — | — | — | — | — | — | — |
| 90/10 | 9 | 0.61 | 13 | 0.57 | 17 | 0.55 | 21 | 0.68 |
| 40/60 | 10 | 0.62 | 14 | 0.41 | 18 | 0.56 | 22 | 0.61 |
| 30/70 | 11 | 0.66 | 15 | 0.45 | 19 | 0.60 | 23 | 0.60 |
| 5/95 | 12 | 0.59 | 16 | 0.45 | 20 | 0.48 | 24 | 0.86 |
| 0/100 | — | — | — | — | — | — | — | — |

What is claimed is:

1. Composition for combating slimes containing as the active compound combination, tetramethylthiuram disulfide and aroyl-ethyl ammonium salts of the formula

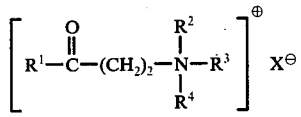

wherein

R[1] is benzoyl or chlorobenzoyl and

R[2], R[3] and R[4] are the same or different and are $C_1$–$C_6$ aliphatic or form together with the nitrogen atom, a heterocyclic group of 5 or 6 members in the ring or a monosubstituted or polysubstituted $C_1$–$C_6$ aliphatic or a heterocyclic ring formed together with said nitrogen atom said heterocyclic ring having 5 or 6 members wherein the substituent is fluorine, chlorine, bromine, iodine, a hydroxyl group, a nitro group, a $C_1$–$C_6$ alkyl radical, a $C_1$–$C_6$ halogen alkyl radical or a $C_1$–$C_6$ straight or branched alkoxy group, and X is an anion of an inorganic or organic acid, the weight ratio of the aroyl-ethyl-ammonium salt to the tetramethylthiuram disulfide being between 1:0.01 and 1:99.

2. Composition of claim 1 wherein the weight ratio of the aroyl-ethyl-ammonium salt to the tetramethylthiuram disulfide is between 1:0.1 and 1:9.

3. Composition of claim 1 wherein the active compound combination is 40 to 52 parts by weight of aroly-ethyl-ammonium chloride and 60 to 48 parts by weight of tetramethylthiuram disulfied.

4. Process for combating slimes wherein an active compound combination of claim 1 is applied to slimes or their habitat.

* * * * *